(12) United States Patent
Minami (10) Patent No.: US 6,685,631 B2
(45) Date of Patent: Feb. 3, 2004

(54) ELECTRONIC ENDOSCOPE SYSTEM HAVING VARIABLE POWER FUNCTION

(75) Inventor: Itsuji Minami, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 24 days.

(21) Appl. No.: 10/095,107

(22) Filed: Mar. 12, 2002

(65) Prior Publication Data

US 2002/0133059 A1 Sep. 19, 2002

(30) Foreign Application Priority Data

Mar. 16, 2001 (JP) ........................................ 2001-075999

(51) Int. Cl.[7] ................................................ A61B 1/05
(52) U.S. Cl. ..................... 600/168; 600/117; 348/240.1
(58) Field of Search ................................. 600/160, 109, 600/118, 168, 117; 348/65, 71, 74, 76, 347, 240.1

(56) References Cited

U.S. PATENT DOCUMENTS 6,151,070 A  * 11/2000 Sato et al. .............. 348/240.99
6,204,880 B1 *  3/2001 Nishimura ............. 348/240.99
6,348,948 B1 *  2/2002 Kyuma ........................ 348/360
6,396,538 B1 *  5/2002 Kobayashi et al. ..... 348/240.99
6,425,858 B1 *  7/2002 Minami ....................... 600/168
6,508,760 B2 *  1/2003 Yamanaka et al. .......... 600/168
2001/0040630 A1 * 11/2001 Matsuzaka ................... 348/240

FOREIGN PATENT DOCUMENTS

EP          0 795 769      *  9/1997
JP          11-136562      *  5/1999

* cited by examiner

*Primary Examiner*—John P. Leubecker
(74) *Attorney, Agent, or Firm*—Snider & Associates; Ronald R. Snider (57) ABSTRACT

To provide an electronic endoscope system provided with an objective optical system for optically magnifying an image to be observed by using a variable power lens and an electronic zoom IC circuit for electronically magnifying an image obtained by a CCD. A depth of field at the time of switching between optical variable power and electronic variable power is set at an arbitrary value by key operation etc. of a control panel of a processor. When the depth of field becomes a setting value, for example, 16 mm (lens position before Near end), during the operation of optical variable power based on the operation of a variable power switch, electronic variable power is executed by the electronic zoom IC circuit. Thereby, an enlarged image in which the depth of a subject to be observed with irregularities is properly in focus can be obtained.

7 Claims, 6 Drawing Sheets

FIG.1

FIG. 2A Far END

FIG. 2B Near END

ELECTRONIC ENDOSCOPE SYSTEM HAVING VARIABLE POWER FUNCTION

BACKGROUND OF THE INVENTION

This application claims the priority of Japanese Patent Applications No. 2001-75999 filed on Mar. 16, 2001 which is incorporated herein by reference.

1. Field of the Invention

The present invention relates to variable power operation control of an electronic endoscope system capable of observing an optical enlarged image using a moving lens and capable of forming an electronic enlarged image by signal processing.

2. Description of the Related Art

In recent years, in an electronic endoscope system or the like, a moving lens for variable power has been disposed in an objective lens system in a scope distal-end portion, and this moving lens has been driven by an actuator or the like, by which an image of a subject to be observed has been enlarged optically. This optically enlarged image is picked up by an image pick-up element such as a CCD (Charge Coupled Device), and various types of image processings are performed by a processor based on the output signal from the CCD, by which an enlarged image of a subject to be observed is displayed on a monitor. In such an optical variable power mechanism, an observed image can be enlarged up to about 70 to 100 times.

On the other hand, conventionally, the image obtained by the CCD is enlarged electronically by picture element interpolation processing etc. of an electronic variable power circuit. According to this, the optically enlarged image can be further enlarged and displayed on the monitor for observation.

In the above-described electronic endoscope system having a variable power function, it has been proposed a technology in which a common variable power switch provided, for example, in an endoscope operating section is used to operate optical variable power and electronic variable power in connection with each other. Specifically, after the variable power switch is operated to move the moving lens to an enlargement end (Near end) by optical variable power, the variable power is automatically shifted to electronic variable power to form a further enlarged image by signal processing. Thereby, a particular portion of an affected part etc. can be observed rapidly with a satisfactory magnification.

However, in the conventional optical variable power mechanism using the moving lens, the depth of field decreases with increasing enlargement ratio, which presents a problem in that, for example, for a subject to be observed having irregularities, there is a case where the whole of the subject in the depth direction cannot be displayed properly. This phenomenon will be described now with reference to FIGS. 7 and 8.

Figure 7:
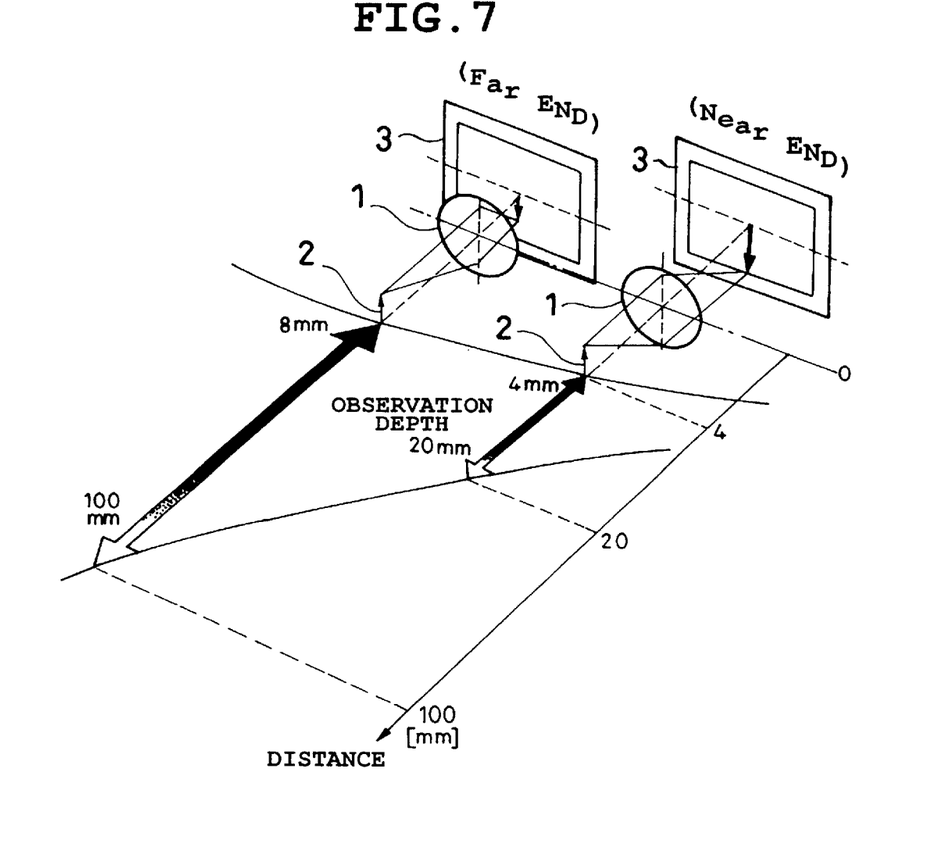
FIG. 7 is an explanatory view showing a depth of field changed by an optical variable power mechanism provided in an endoscope.

In FIG. 7, the left-hand side view shows a state in which when a movable lens 1 lies at the Far end, the proximal end, a subject to be observed 2 forms an image on a CCD image pick-up surface 3, and the right-hand side view shows an image formation state at the time when the moving lens 1 is moved to the Near side, the enlargement side. In FIG. 7, since the moving lens 1 is set at a position of distance 0, at the time of enlargement, the image pick-up surface 3 is drawn so as to be shifted rearward. Actually, the moving lens 1 moves forward. When the optical enlargement is not made as shown in the left-hand side view of FIG. 7, the focus is sharpened, for example, at a distance of 8 to 100 mm, and the depth of field is 92 mm. Whereas, when the optical enlargement is made as shown in the right-hand side view in FIG. 7, the focus is sharpened at a distance of 4 to 20 mm, and the depth of field is 16 mm.

Figure 8:
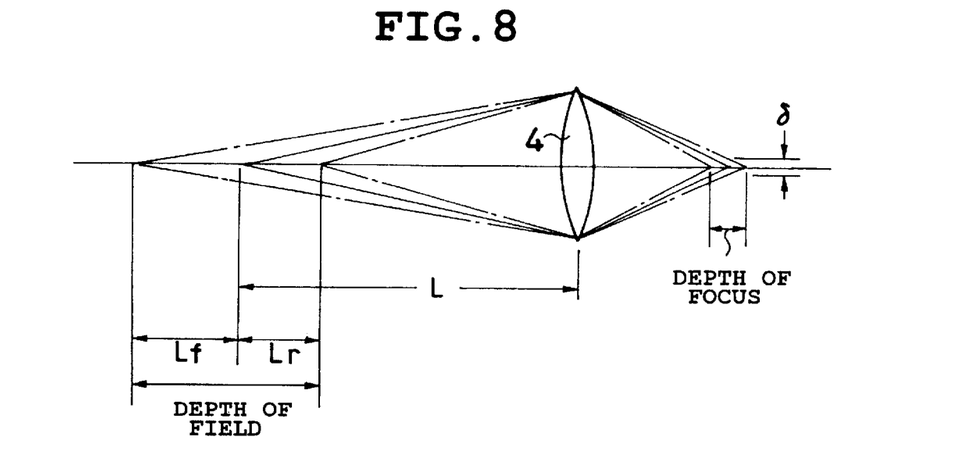
FIG. 8 is an explanatory view of the depth of field of a lens.

FIG. 8 is an explanatory view of the depth of field. Taking the focal length of a lens 4 as f, the F number as $F_N$, the allowable blur circle as $\delta$, and the distance of subject to be observed as L, the rear depth of field $L_r$ and the front depth of field $L_f$ are expressed as follows:

$$L_r = (\delta \cdot F_N \cdot L^2)/(f^2 - \delta \cdot F_N \cdot L) \quad (1)$$

$$L_f = (\delta \cdot F_N \cdot L^2)/(f^2 + \delta \cdot F_N \cdot L) \quad (2)$$

The depth of field of this lens 4 is a value obtained by summing up the rear depth of field $L_r$ and the front depth of field $L_f$, that is, $L_r + L_f$. The depth of focus is $2\delta \cdot F_N$.

The aforementioned depth of field explained in FIG. 7 is also the above-described value of $L_r + L_f$, and the range in which the focus is sharp is 92 mm at the Far end and 16 mm at the Near end. In the configuration of variable power objective optical system now used for an endoscope, the depth of field decreases as the image is enlarged. Therefore, in the case where a subject to be observed having irregularities is observed, the depth of field becomes shallow (short), so that a blur occurs somewhere in the depth direction. When the subject to be observed is caught in a state of shallow depth of field is enlarged electronically, the blur in the depth direction is also enlarged, which presents a problem in that the whole of the subject to be observed cannot be displayed and observed with high picture quality.

SUMMARY OF THE INVENTION

The present invention has been achieved to solve the above problems, and accordingly an object thereof is to provide an electronic endoscope system having a variable power function, which is capable of arbitrarily setting the depth of field at the time of shifting to electronic variable power to eliminate a blur in the depth direction of electronically enlarged image.

To attain the above object, an electronic endoscope system having a variable power function, comprising: an objective optical system for optically magnifying an image to be observed by using a variable power lens; an electronic variable power circuit for electronically magnifying an image obtained via an image pick-up element by signal processing; common variable power operating means for operating the optical variable power and electronic variable power; switching point setting means for setting a depth of field at the switching time between the optical variable power and electronic variable power at an arbitrary value; and a control circuit which continuously operates optical variable power and electronic variable power based on the operation of the variable power operating means, and controls the switching between optical variable power and electronic variable power with the arbitrary setting value of depth of field being a switching point. This control circuit sets the depth of field by changing it into the position of variable power lens.

Also, another invention is characterized in that an enlargement ratio, not a depth of field, is used as a control element for switching between optical variable power and electronic variable power, and when the enlargement ratio becomes an arbitrary setting value, transfer from optical enlargement to electronic enlargement is effected. Specifically, a change in depth of field can also be detected by a change in enlargement ratio, and the value of depth of field can be controlled by the value of enlargement ratio.

According to the above-described configuration, the control for transferring to electronic variable power is carried out by the set value of depth of field, for example, in a field depth preference mode, not in an ordinary mode in which electronic variable power is effected when the variable power lens moves to the Near end. In this field depth preference mode, if the value of depth of field at the time of transfer to electronic variable power is set by key operation on a control panel etc. of a processor, the position (for example, $a_1$) of moving lens corresponding to the value of depth of field is calculated, and this lens position $a_1$, is stored and held in a memory etc.

When operation is performed in the enlargement direction by using the variable power switch, optical variable power is first effected. If the enlargement operation is further performed after the moving lens has reached the position $a_1$, the optical variable power operation is stopped, and subsequently electronic variable power is executed. Therefore, when electronic enlargement is made, an arbitrarily set depth of field is maintained. Therefore, even for a subject to be observed with a depth, an enlarged image in which the focus is sharp in a wide range can be displayed and observed.

DETAILED DESCRIPTION OF THE PREFERRED EMBODIMENTS

Figure 1:
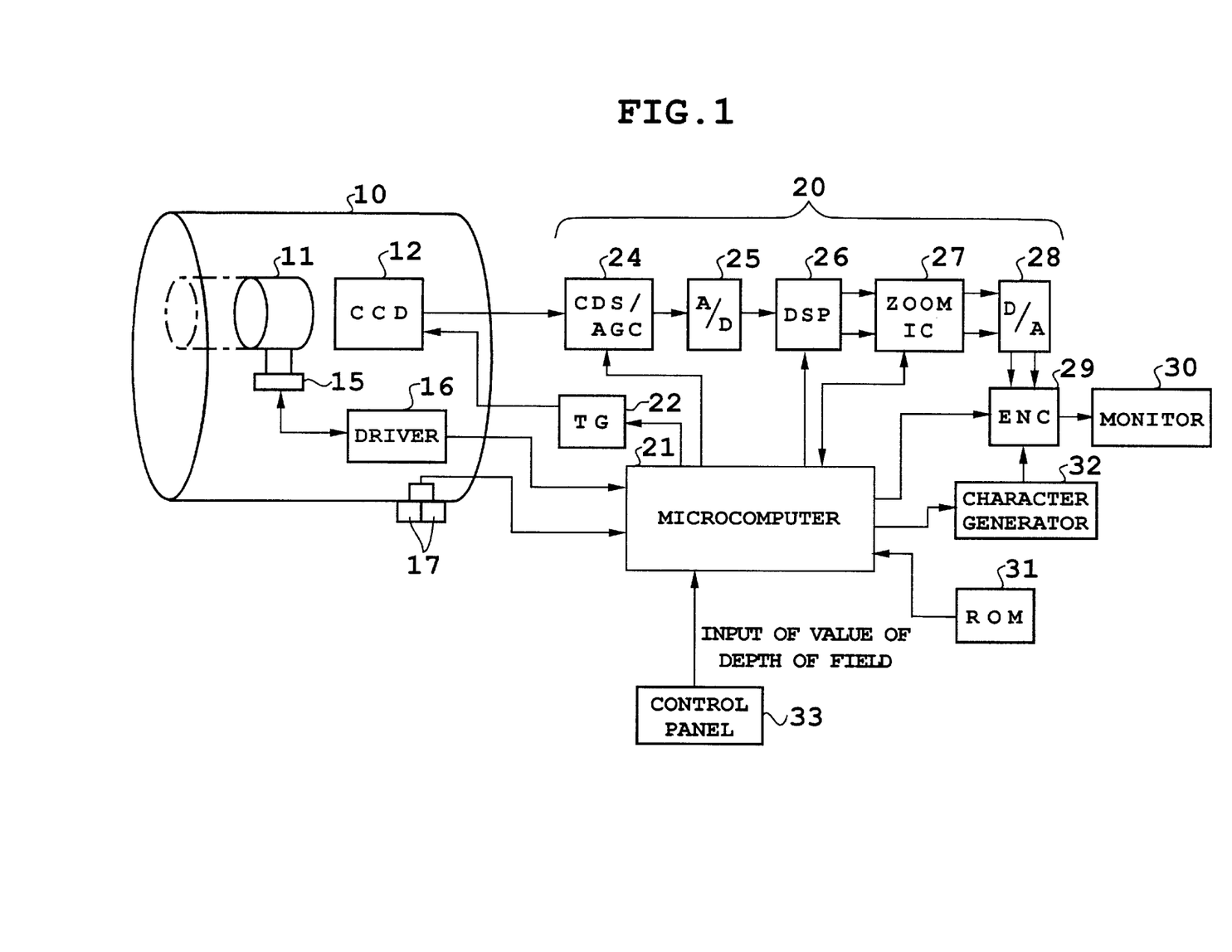
FIG. 1 is a block diagram showing a configuration of an electronic endoscope system having a variable power function in accordance with an embodiment of the present invention.

FIG. 1 shows a configuration of an electronic endoscope system in accordance with an embodiment. In FIG. 1, in a distal end portion of an electronic endoscope 10, an objective optical system 11 having a variable power lens is provided, and a CCD 12 is disposed so that the image pick-up surface coincides with the image forming position of the objective optical system 11. The objective optical system 11 and the CCD 12 are configured, for example, as shown in FIG. 2.

Figure 2A:
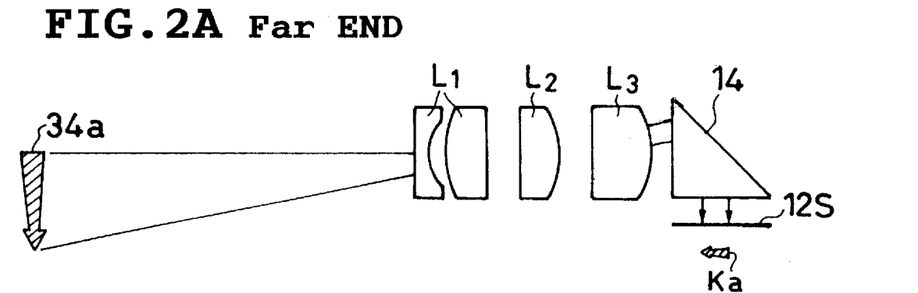
FIG. 2A is a view showing a configuration of an objective optical system of an embodiment and a state of image formation at the Far end.
Figure 2B:
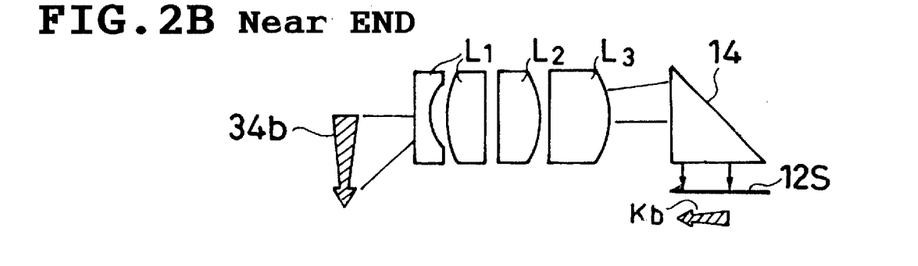
FIG. 2B is a view showing a configuration of an objective optical system of an embodiment and a state of image formation at the Near end.

As shown in FIGS. 2A and 2B, the objective optical system 11 is made up of a fixed first lens (group) $L_1$, a movable second lens $L_2$ mainly performing a variable power function, and a movable third lens (group) $L_3$ performing other functions (for example, a change in image surface curvature characteristics). At the rear of the third lens $L_3$, an image pick-up surface 12S of the CCD 12 is disposed via a prism 14. According to the above-described objective optical system 11, both of the second lens $L_2$ and the third lens $L_3$ are moved relatively in the optical axis direction, by which the magnification of image can be changed, and also, for example, the image surface curvature characteristics can be changed. In this example, by moving the second lens $L_2$ forward together with the third lens $L_3$, the image is enlarged.

In FIG. 1, there are provided an actuator for driving the second lens $L_2$ and the third lens $L_3$ of the objective optical system 11 and a position detector 15. For this actuator, means in which a linear transmission member is rotationally driven by a linear actuator or motor, and this rotational motion is converted into linear motion to move the lenses $L_2$ and $L_3$ can be used. This actuator and position detector 15 is provided with a driver 16 for detecting the lens position and for performing variable power operation. Also, in the operating section etc. of the electronic endoscope 10, a variable power switch (double acting switch) 17 is disposed which performs operation in the Near (enlargement) direction and the Far (reduction) direction for both optical enlargement and electronic enlargement.

On the other hand, in a processor 20, there are provided a microcomputer 21 and a timing generator (TG) 22. The microcomputer 21 controls the aforementioned actuator driver 16, controls optical variable power and electronic variable power based on the operation signal sent from the variable power switch 17, and performs other various kinds of control operations. The timing generator 22 supplies a control signal for reading an image pick-up signal to the CCD 12.

Also, as a processing system for a video signal, a CDS (Correlation Double Sampling)/AGC (Automatic Gain Control) circuit 24, an A/D converter 25, a DSP (Digital Signal Processor) 26 for performing various digital processing such as white balance, gamma correction, and contour correction, an electronic zoom IC circuit 27, which is an electronic variable power circuit, a D/A converter 28, and an encoder (ENC) 29 for performing output processing matching the display type are disposed. The output of this encoder 29 is supplied to a monitor 30. In the electronic zoom IC circuit 27, the video signal obtained by the DSP 26 is stored in a memory, and an enlarged image can be formed by interpolation processing of picture element in the horizontal and vertical directions.

Further, the processor 20 is provided with a ROM (Read Only Memory) 31 and a character generator 32 for producing various characters. The ROM 31 stores values of depth of field and enlargement ratio, data for forming other characters, and arithmetic data etc. for determining the position of the moving lens $L_2$ (or $L_3$) corresponding to the depth of field. By this character generator 32, a character image such as the depth of field and enlargement ratio during the variable power operation for displaying on the monitor is formed.

Also, by operating various keys provided on a control panel (operating section) 33 of the processor 20, the microcomputer 21 converts the value of depth of field in the field depth preference mode into the lens position and sets it. The setting of this value is performed by displaying, for example, the field depth preference mode setting screen on the monitor and inputting the depth of field by a numerical value, or by checking the optimum depth width in which the focus is sharp on the actual image of the subject to be observed while being enlarged which is displayed on the monitor and automatically judging the value of depth of field at this time by any decision operation. The microcomputer 21 calculates and judges the position of the moving lens $L_2$ corresponding to the set value of depth of field, and stores the position data in the memory in the microcomputer 21 as the position of switching from optical variable power to electronic variable power.

Figure 3A:
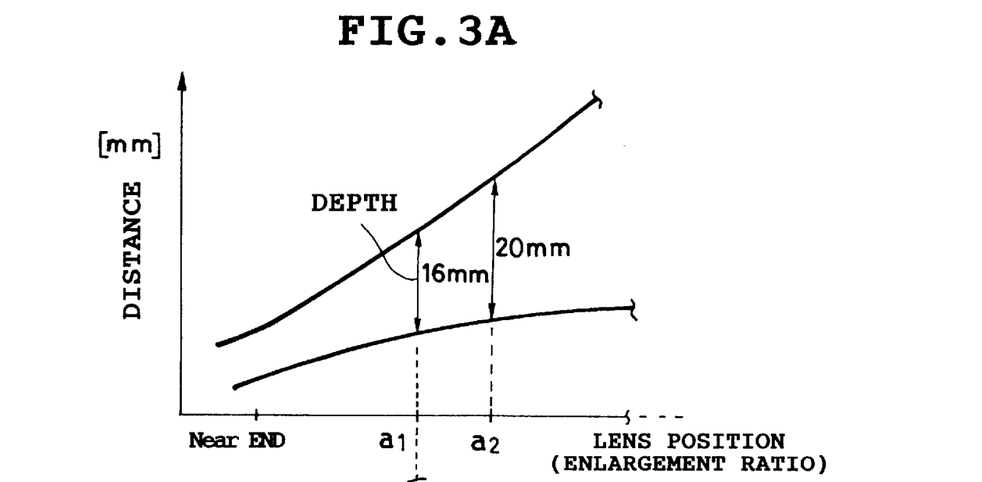
FIG. 3A is a graph showing a depth of field set as a switching position by an objective optical system of an embodiment.
Figure 3B:
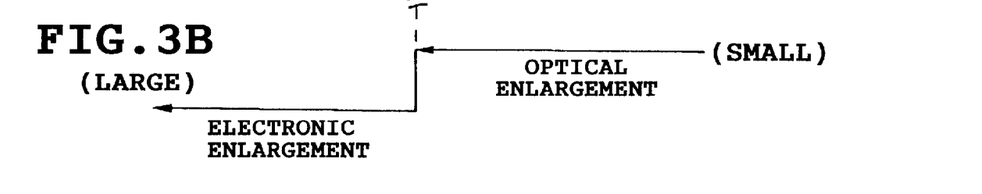
FIG. 3B is an explanatory view showing a switching position from optical variable power to electronic variable power in FIG. 3A.

FIGS. 3A and 3B show the switching position from optical variable power to electronic variable power in this example. For example, assuming that the depth of field at the time of switching is 16 mm, a position $a_1$ before the Near end on the abscissa is calculated as the position of the moving lens $L_2$ corresponding the depth of field, and this position $a_1$ is set. Further, when the depth of field is 20 mm, the position $a_2$ is set.

The embodiment is configured as described above, and the operation there of will now be explained. In this system, when the variable power switch 17 in the operating section of the electronic endoscope 10 is operated, the second lens $L_2$ (and the third lens $L_3$) are moved by the driver 16 and the actuator 15. Thus, an image enlarged from the basic image can be obtained by the focusing toward the Near end, and an image reduced to the basic image can be obtained by the focusing toward the Far end, and these images are picked up by the CCD 12.

Specifically, when the variable power switch 17 is not operated in an ordinary mode, the moving second lens $L_2$ (and $L_3$) are disposed at the Far end, and a subject to be observed 34a at a long distance forms an image Ka on the image pick-up surface 12S as shown in FIG. 2A. If the enlargement operation is performed by the variable power switch 17, the movable second lens $L_2$ moves forward as shown in FIG. 2B, and at the time of the maximum enlargement (Near end), a subject to be observed 34b at a short distance forms an image Kb.

The signal sent from the CCD 12 is read by a read signal of the timing generator 22. After the correlation double sampling and amplification processing have been performed in the CDS/AGC circuit 24, the signal is subjected to various processing by the DSP 26 as a digital signal. The video signal formed in this manner is outputted on the monitor 30 via the electronic zoom IC circuit 27 and the encoder 29. When optical magnification is performed as described above, an optically enlarged image of the subject to be observed is displayed on the monitor 30. When the enlargement operation of the variable power switch 17 is further performed in the ordinary mode, electronic enlargement processing is performed by the electronic zoom IC circuit 27 in the lens position (Near end) shown in FIG. 2B, and an image of the subject to be observed further enlarged from the optically enlarged image is displayed on the monitor 30.

Figure 4:
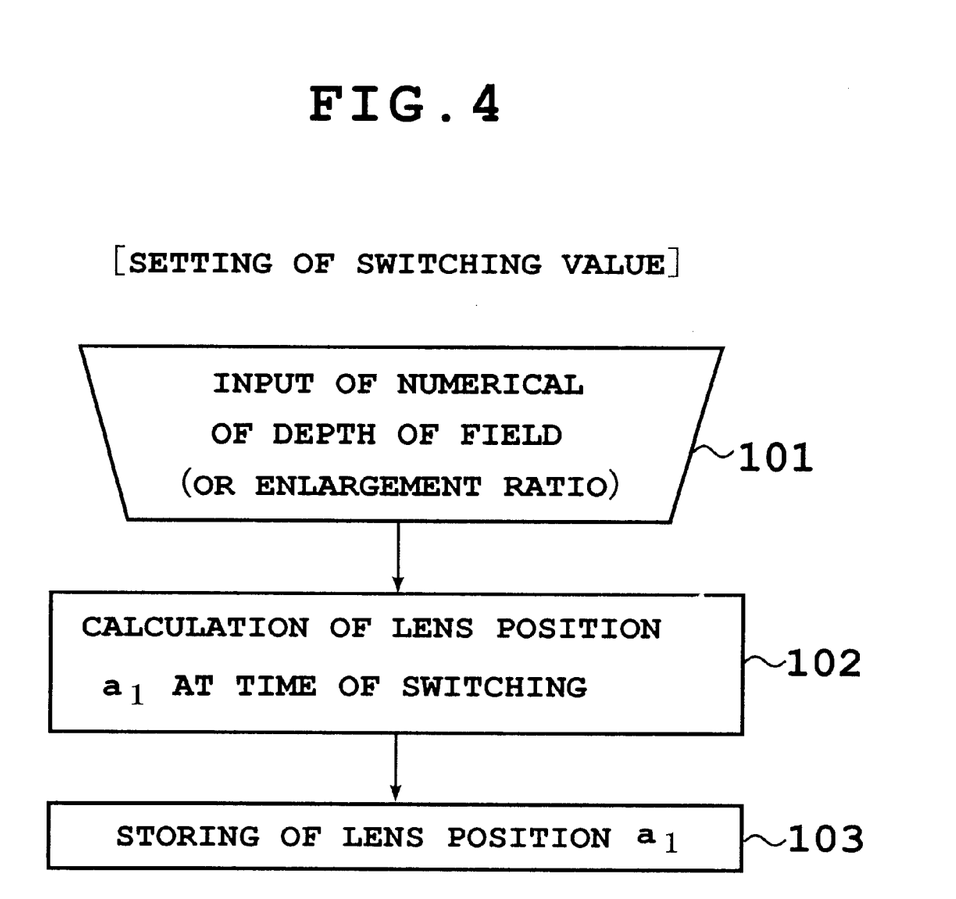
FIG. 4 is a flowchart showing a setting operation for a depth of field or enlargement ratio in an embodiment.

On the other hand, in this system, the field depth preference mode can be executed in addition to the above-described ordinary mode. In the field depth preference mode, first, the setting of switching value (depth of field) shown in FIG. 4 is performed. Referring to FIG. 4, when the value of depth of field is inputted by a key etc. of the control panel 33 in Step 101, the position of the moving lens $L_2$ corresponding to the value of depth of field is calculated as described above in Step 102. In Step 103, for example, $a_1$ shown in FIGS. 3A and 3B is stored and held in a memory etc. as the switching position.

Figure 5:
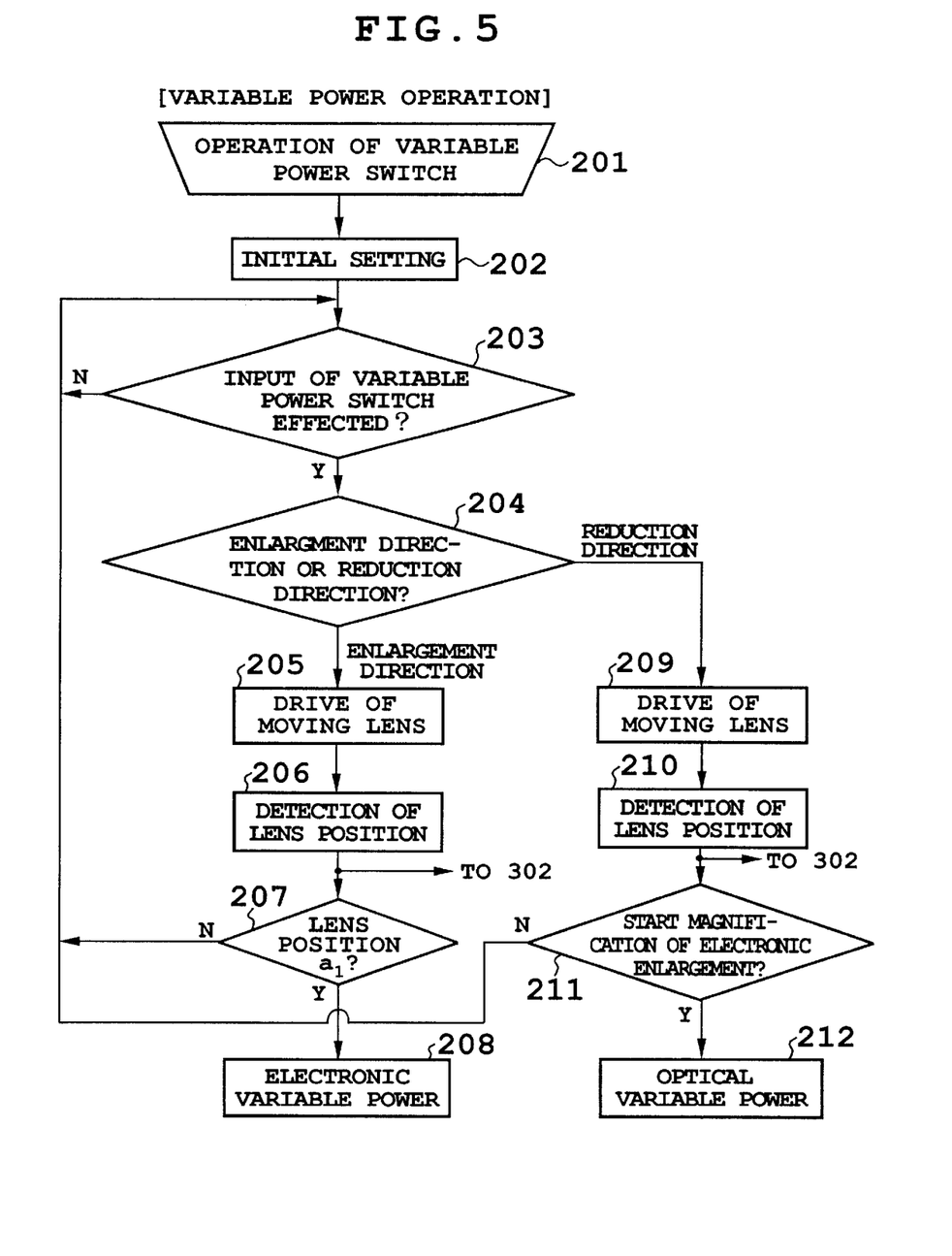
FIG. 5 is a flowchart showing a variable power operation in an embodiment.

FIG. 5 shows a variable power processing operation in the field depth preference mode. When the variable power switch 17 is operated in Step 201, initial setting for setting the lens positions of the moving lenses $L_2$ and $L_3$ at the Far end is performed in Step 202. In the next step 203, judgment is made whether or not the input (variable power operation) of the variable power switch 17 has been effected. If the judgment result is YES, it is judged whether the change in power is in the enlargement direction or in the reduction direction in Step 204. When the operation of the variable power switch 17 is in the enlargement direction, the drive of the second lens $L_2$ and the third lens $L_3$ is accomplished via the driver 16 in Step 205, and the position of the second lens $L_2$ is detected in Step 206.

In the next step 207, it is judged whether or not the position of the second lens $L_2$ has reached $a_1$. If the judgment result is YES, in Step 208, the second lens $L_2$ and the third lens $L_3$ are stopped, and electronic enlargement processing by using the electronic zoom IC circuit 27 is started. This start magnification of electronic enlargement is stored and held in a memory etc. in the microcomputer 21. Specifically, for the optical image with a depth of field of 16 mm, an electronically enlarged image is formed by the picture element interpolation processing in the horizontal and vertical directions, and this enlarged image is displayed on the monitor 30.

Even when it is judged that the operation of the variable power switch 17 is in the reduction direction in the above-described step 204, the drive of the lenses $L_2$ and $L_3$ and the position detection of the second lens $L_2$ are accomplished in Steps 209 and 210, respectively. In the next step 211, judgment is made whether or not the magnification has become the start magnification of electronic enlargement. If the judgment result is YES, in Step 212, the electronic reduction processing using the electronic zoom IC circuit 27 is stopped, and the drive of the second lens $L_2$ and the third lens $L_3$ in the reduction direction is started. Specifically, the reduction operation of optical variable power from the Near end toward the Far end is performed.

Figure 6:
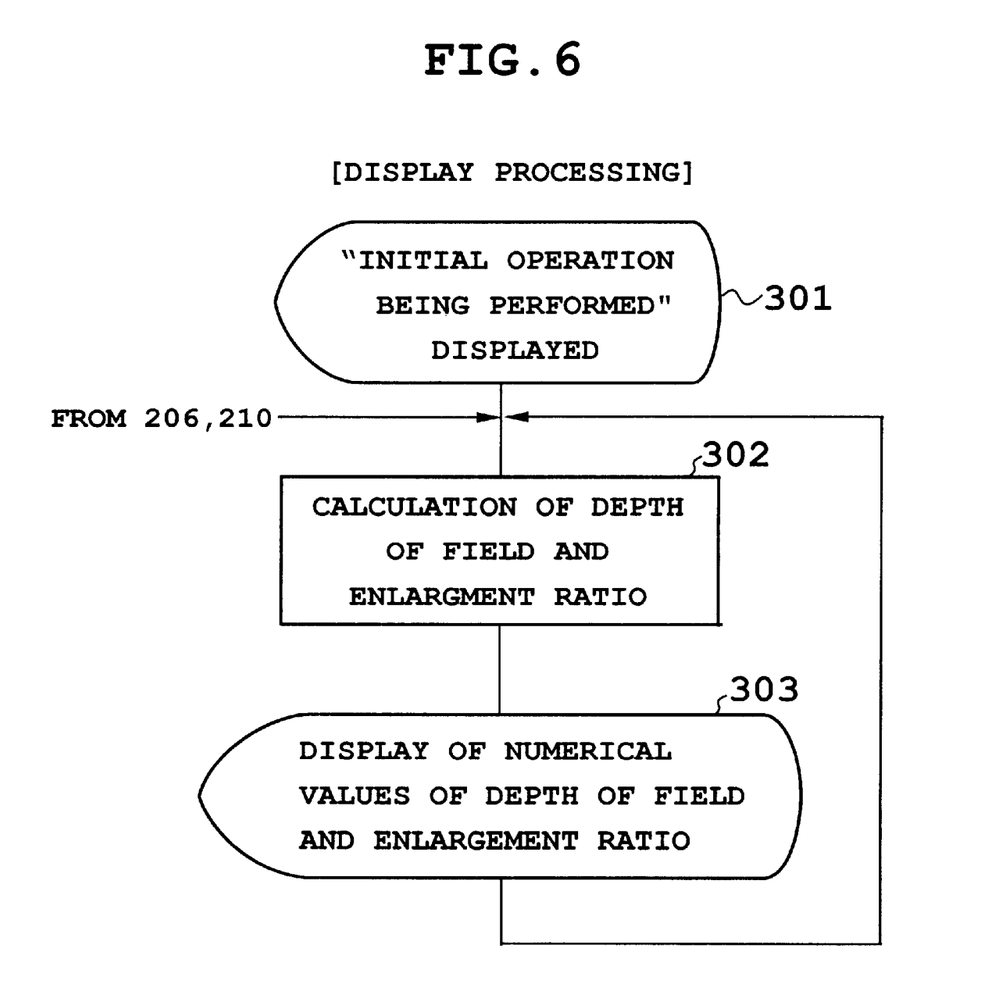
FIG. 6 is a flowchart showing a character display operation in an embodiment.

FIG. 6 shows a display processing of image pick-up condition data displayed on the monitor 30. After the power source of the processor 20 is turned on, "Initial operation being performed" is displayed in Step 301. Specifically, it is displayed that the initial setting operation of lens position in Step 202 in FIG. 5 is being performed. In the next step 302, based on the position detection of the second lens $L_2$ in Steps 206 and 210 in FIG. 5, the present depth of field and enlargement ratio are calculated from this lens position, and the depth of field and enlargement ratio are displayed on the monitor 30 in Step 303.

Thus, in the field depth preference mode of this example, when the depth of field set by the variable power objective optical system 11 becomes a value deeper than the switching value of the ordinary mode, for example, 16 mm, that is, when the second lens $L_2$ is moved to the position $a_1$, optical variable power and electronic variable power are switched, and moreover the depth of field can be set arbitrarily. Therefore, even for a subject to be observed with a depth or great irregularities, the focus is sharpened in the whole thereof, so that an electronically enlarged image with high picture quality can be displayed and observed.

Although the switching between optical variable power and electronic variable power is performed by the value of depth of field in the above-described embodiment, the switching between optical variable power and electronic variable power can be performed indirectly by the value of enlargement ratio by detecting the depth of field as a change in enlargement ratio. Specifically, in Step 101 in FIG. 4, the enlargement ratio is inputted, and the lens position corresponding to the enlargement ratio is calculated and set (Steps 102 and 103). Thereby, like the above-described procedure, an optically enlarged image obtained with a depth of field suitable for the subject to be observed can be electronically enlarged.

As described above, according to the present invention, the switching between optical variable power and electronic variable power is controlled with an arbitrary setting value of depth of field or enlargement ratio being a switching point. Therefore, in the electronically enlarged image, the depth of field corresponding to a different depth of the subject to be observed with irregularities is set freely, and thus an enlarged image of the subject to be observed, in which a blur in the depth direction has been eliminated, can be displayed and observed properly.

What is claimed is:

1. An electronic endoscope system having a variable power function, comprising:

an objective optical system for optically magnifying an image to be observed by using a variable power lens;

an electronic variable power circuit for electronically magnifying an image obtained via an image pick-up element by signal processing;

common variable power operating means for operating optical variable power and electronic variable power;

switching point setting means for setting a depth of field at the switching time between optical variable power and electronic variable power at an arbitrary value;

a control circuit which continuously operates optical variable power and electronic variable power based on the operation of said variable power operating means, and controls the switching between optical variable power and electronic variable power with said arbitrary value of a depth of field being a switching point; and wherein said switching point setting means sets the depth of field at the arbitrary value by an operating member on an operating section.

2. The electronic endoscope system having a variable power function according to claim 1, wherein said control circuit sets said depth of field by changing the depth of field corresponding to the position of said variable power lens.

3. The electronic endoscope system having a variable power function according to claim 1, wherein the present value of said depth of field is displayed on a monitor.

4. The electronic endoscope system having a variable power function comprising:

an objective optical system for optically magnifying an image to be observed by using a variable power lens;

an electronic variable power circuit for electronically magnifying an image obtained via an image pick-up element by signal processing;

common variable power operating means for operating optical variable power and electronic variable power;

switching point setting means for setting a depth of field at the switching time between optical variable power and electronic variable power at an arbitrary value;

a control circuit which continuously operates optical variable power and electronic variable power based on the operation of said variable power operating means, and controls the switching between optical variable power and electronic variable power with said arbitrary value of a depth of field being a switching point; and wherein the control for switching between optical variable power and electronic variable power is carried out in a depth field preference mode by the arbitrary value of depth of field, and said field depth preference mode can be set separately from an ordinary mode in which after said variable power lens is moved to a Near end, electronic variable power is executed.

5. An electronic endoscope system having a variable power function, comprising:

an objective optical system for optically magnifying an image to be observed by using a variable power lens;

an electronic variable power circuit for electronically magnifying an image obtained via an image pick-up element by signal processing;

common variable power operating means for operating optical variable power and electronic variable power;

switching point setting means for setting a depth of field of view at an arbitrary value by setting an enlargement ratio at the switching time between optical variable power and electronic variable power at an arbitrary value;

a control circuit which continuously operates optical variable power and electronic variable power based on the operation of said variable power operating means, and controls the switching between optical variable power and electronic variable power with said arbitrary value of enlargement ratio being a switching point; and wherein said switching point setting means sets the depth of field at an arbitrary value by an operating member on an operating section.

6. The electronic endoscope system having a variable power function according to claim 5, wherein the present value of an enlargement ratio is displayed on a monitor.

7. The electronic endoscope system having a variable power function comprising:

an objective optical system for optically magnifying an image to be observed by using a variable power lens;

an electronic variable power circuit for electronically magnifying an image obtained via an image pick-up element by signal processing;

common variable power operating means for operating optical variable power and electronic variable power;

switching point setting means for setting an enlargement ratio at the switching time between optical variable power and electronic variable power at an arbitrary value;

a control circuit which continuously operates optical variable power and electronic variable power based on the operation of said variable power operating means, and controls the switching between optical variable power and electronic variable power with said arbitrary setting value of enlargement ratio being a switching point; and wherein the control for switching between optical variable power and electronic variable power is carried out in a depth field preference mode by the arbitrary value of enlargement ratio, and said field depth preference mode can be set separately from an ordinary mode in which after said variable power lens is moved to the Near end, electronic variable power is executed.

* * * * *